United States Patent [19]

Ouan et al.

[11] Patent Number: 4,739,054

[45] Date of Patent: Apr. 19, 1988

[54] TRIAZOLOPYRIMIDINE EXTRACTANTS

[75] Inventors: Peter M. Ouan, Rochdale; Anthony J. Nelson, Manchester, both of England

[73] Assignee: Imperial Chemical Industries PLC, London, England

[21] Appl. No.: 28,747

[22] Filed: Mar. 23, 1987

Related U.S. Application Data

[62] Division of Ser. No. 806,458, Dec. 9, 1985, Pat. No. 4,675,172.

[30] Foreign Application Priority Data

Dec. 12, 1984 [GB] United Kingdom ................ 8431305

[51] Int. Cl.$^4$ .................... C07D 403/04; C22B 3/00
[52] U.S. Cl. .................................................. 544/263
[58] Field of Search ........................................ 544/263

[56] References Cited

FOREIGN PATENT DOCUMENTS 0112617  7/1984  European Pat. Off. .

OTHER PUBLICATIONS

Birr, *Stabilization of Photographic Silver Halide Emulsions,* (1974: Focal Press Ltd; New York), p. 209.
Chemical Abstracts, vol. 54, no. 22, Nov. 1960.

*Primary Examiner*—Donald G. Daus
*Assistant Examiner*—Mark W. Noel
*Attorney, Agent, or Firm*—Cushman, Darby & Cushman

[57] ABSTRACT

Metal values, particularly copper values, are extracted from aqueous solutions containing halide or pseudohalide anion using 6, 7 substituted triazolopyrimidine wherein the 6-substituent is a group —CO—OR1 where R1 is a hydrocarbyl group containing from 1 to 35 carbon atoms, preferably an alkyl group and wherein the 7-substituent (R2) is hydrogen or a hydrocarbyl group containing from 1 to 35 atoms wherein R1 and R2 taken together contain a total of from 5 to 35 saturated carbon atoms.

7 Claims, No Drawings

TRIAZOLOPYRIMIDINE EXTRACTANTS

This is a division of application Ser. No. 806,458, filed Dec. 9, 1985 now U.S. Pat. No. 4,675,172.

This invention relates to a process for the extraction of metal values from aqueous solutions of metal salts, and in particular to a process for the extraction of metal values from aqueous solutions in the presence of halide anions.

The use of solvent extraction techniques for the hydrometallurgical recovery of metal values from metal ores has been practised commercially for a number of years. For example copper may be recovered from oxide ores or from ore tailings by treating the crushed ore with sulphuric acid to give an aqueous solution of copper sulphate which is subsequently contacted with a solution in a water-immiscible organic solvent of a metal extractant whereby the copper values are selectively extracted into the organic phase.

The application of solvent extraction techniques to aqueous solutions containing halide anions however has presented numerous technical problems. For example copper bearing sulphur-containing ores such as chalcopyrite may be leached using ferric chloride or cupric chloride solutions, but the solvent extraction of the resultant leach solutions presents formidable difficulties.

The present invention provides a process for the extraction of metal values from aqueous solutions containing halide ions by the use of metal extractants whose several properties meet the stringent requirements imposed on the extractant by the system.

According to the present invention there is provided a process for extracting metal values from aqueous solutions of metal salts containing halide or pseudo halide anions which comprises contacting the aqueous solution with a solution in a water-immiscible organic solvent of a triazolopyrimidine of formula:

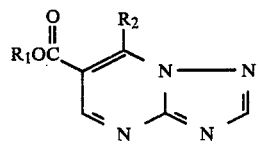

(1)

wherein $R_1$ is a hydrocarbyl group containing from 1 to 35 saturated carbon atoms and $R_2$ is hydrogen or a hydrocarbyl group containing from 1 to 35 carbon atoms, provided that $R_1$ and $R_2$ taken together contain a total of from 5 to 35 saturated carbon atoms.

$R_1$ is preferably an alkyl group or a substituted alkyl group. As optional substituents which may be present in the the alkyl group there may be mentioned, halogen, for example chlorine, nitro, cyano, hydroxy, alkoxy, aryl, aryloxy, alkoxycarbonyl, alkylcarbonyloxy. $R_1$ preferably contains from 5 to 35 saturated carbon atoms, for example from 16 to 35 saturated carbon atoms and especially from 16 to 24 saturated carbon atoms, subject to the proviso that $R_1$ and $R_2$ together contain a total of from 5 to 35 saturated carbon atoms.

$R_2$ may for example be hydrogen; or any of the preferred groups mentioned above in respect of $R_1$; or an aryl group. Suitable aryl groups include phenyl and substituted phenyl. As examples of substituents which may be present in the phenyl group there may be mentioned one or more of halogen atoms, aryl groups, alkoxy groups, aryloxy groups, cyano groups and nitro groups and especially alkyl groups such as methyl and t-butyl.

Preferably $R_1$ and $R_2$ taken together contain a total of from 16 to 35 saturated carbon atoms.

The term "saturated carbon atoms" as used herein means carbon atoms each of which is attached to four other atoms and excludes for example carbon atoms present in an aromatic ring.

To achieve good solubility of the compound in preferred organic solvents, $R_1$ and/or $R_2$ (if an alkyl group) respectively are preferably branched alkyl groups or a mixture (including an isomeric mixture) of branched alkyl groups. Solubility of the metal complex in the preferred solvents will be improved if $R_2$ contains more than 1 saturated carbon atom.

Highly branched alkyl groups may be usefully derived from branched alcohols prepared by the Guerbet and Aldol condensations. Such alcohols are characterised by branching at the position beta to the hydroxyl group and have the general formula:

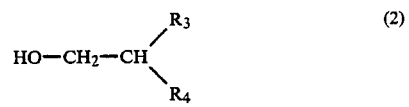

(2)

wherein $R_3$ and $R_4$ are both alkyl groups and $R_3$ contains two fewer carbon atoms than $R_4$. $R_3$ and $R_4$ may be straight chain or branched chain alkyl groups and may be isomeric mixtures of alkyl groups. A mixture of highly branched alcohols may be obtained by Guerbet or Aldol condensations of mixtures of alcohols and aldehydes respectively. By way of example, good solubility in preferred organic solvents is conferred on the triazolopyrimidine compounds wherein $R_1$ is derived from commercial isooctadecanol consisting essentially of a mixture of geometrical isomers of the compound (formula 3):

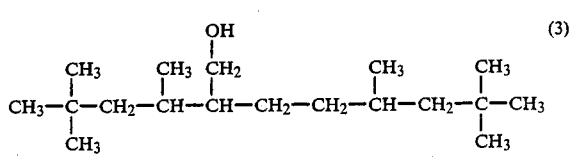

(3)

Suitable groups, $R_1$ also include octyl, nonyl, decyl, dodecyl, tridecyl, pentadecyl, hexadecyl or octadecyl or a higher alkyl group.

The triazolopyrimidines of the present invention may be prepared by conventional means, for example the general method described in Chemical Abstracts Vol 54 (1960) at 11039c followed by appropriate transesterification.

The process of the present invention may be applied to the extraction from aqueous solutions containing halide or pseudohalide ion of any metal capable of forming a stable halide or pseudohalide containing complex with the triazolopyrimidine in the water-immiscible organic solvent. Examples of such metals include copper, cobalt, cadmium and zinc. The process of the present invention is especially suitable for the solvent extraction of copper from aqueous solution obtained by the halide or pseudohalide leaching of sulphur containing ores, for example from solutions obtained by the leaching of ores such as chalcopyrite with aqueous ferric chloride or cupric chloride solutions.

It will be appreciated that the process of the present invention may be incorporated into a wide variety of different methods for the overall recovery of metals from their ores or from other metal-bearing sources. Details of these methods will vary depending on the metal concerned and the nature and composition of the leach solution. By way of example, an integrated process which is especially suitable for leach solutions containing high levels of cupric ion is described in European Patent Publication No. 57797

A typical solvent extraction process for recovering copper from a sulphide or complex sulphide ore involves the following stages:

(1) Leaching of the copper ore with aqueous ferric or cupric chloride solution to obtain an aqueous solution containing copper values;

(2) contacting the aqueous leach solution from stage (1) with a solution in a water-immiscible organic solvent of the triazolopyrimidine whereby at least a proportion of the copper value is extracted into the organic phase in the form of a halide (or pseudo halide) containing complex of the copper with the triazolopyrimidine;

(3) separating the aqueous phase from the water-immiscible organic solvent phase into which the metal has been extracted;

(4) contacting the resultant organic phase with an aqueous strip solution which is water or which contains a reduced concentration of halide (or pseudo halide) ion or copper whereby the halide (or pseudohalide) containing complex of copper with the triazolopyrimidine is rendered unstable and at least a proportion of the copper transfers into the aqueous strip solution; and (5) recovering the purified copper values from the aqueous strip solution, for example by electrowinning.

The extraction process of the present invention is complex, but in general, the extractant appears to form a complex with a divalent metal ion such as cupric up to a level corresponding to one molecule of copper per molecule of extractant. This would correspond to an extraction equation such as the following:

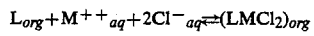

$$L_{org} + M^{++}{}_{aq} + 2Cl^{-}{}_{aq} \rightleftharpoons (LMCl_2)_{org}$$

where M is a divalent metal ion such as copper or zinc.

This equation is a grossly oversimplified representation of a very complex process and is not to be taken as in any way limiting the scope of the present invention, but it serves to illustrate the formation of a neutral organic phase complex of the divalent metal chloride and the extractant (L) which is believed to predominate in the process of the present invention. The equation illustrates the reversible nature of the extraction, whereby the complex of the metal and the extractant in the organic phase can be stripped to return the purified and concentrated metal ion into the aqueous phase. Stripping may take place for example on contact of the organic phase containing the metal/extractant complex with water or with the aqueous solution from the metal recovery (for example electrowinning) stage which is depleted in the metal and in the halide ion.

Since the leach solution contains high levels of iron, it is clearly important that the extractant should show good selectivity for copper over iron. Of particular importance to ensure high purity of the product in the recovery of a metal such as copper from its ores is a good selectivity for copper in the presence of silver and other extractable constituents of the ore.

A further property which is of importance for an extractant in the process of the present invention is the absence of significant protonation by the acidic leach liquor. Such protonation may be represented by an equation such as:

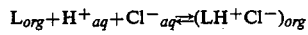

$$L_{org} + H^{+}{}_{aq} + Cl^{-}{}_{aq} \rightleftharpoons (LH^{+}Cl^{-})_{org}$$

where L is the extractant. Such protonation of the ligand carries hydrochloric acid into the organic phase and builds up an excessive chloride ion concentration on the strip side. This ability to extract metal from highly acidic solutions represents a considerable advance over known "ion exchange" reagents which are useful for example for the extraction of copper from the much less aggressive solutions derived from the leaching of copper oxide ores with sulphuric acid.

Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point petroleum fractions (for example kerosene) with varying aromatic content. In general, hydrocarbon solvents having a high aromatic content, for example AROMASOL H which consists essentially of a mixture of trimethylbenzenes and is commercially available from Imperial Chemical Industries PLC (AROMASOL is a trade mark) or SOLVESSO 150 commercially available from Esso (SOLVESSO is a trade mark), provide a higher solubility for the extractant and its metal complex, whilst kerosene having a relatively low aromatic content, for example ESCAID 100 which is a petroleum distillate comprising 20% aromatics, 56.7% paraffins and 23.4% naphthalenes commercially available from Esso (ESCAID is a trade mark) may in certain cases improve the hydrometallurgical performance of the extractant. Factors influencing the solubility of the extractant and its metal complex are complicated, but in general extractants having highly branched substituents and/or an isomeric mixture of substituents have comparatively high solubility. The concentration of the extractant in the water-immiscible organic solvent may be chosen to suit the particular leach solution to be treated. Typical values of extractant concentration in the organic phase are between about 0.1 to 2 Molar, and an especially convenient range is from 0.2 to 0.6 Molar in the organic solvent.

Certain triazolopyrimidines for use in the present invention are novel compounds and the present invention includes such novel compounds.

The invention is illustrated by the following Example in which all parts and percentages are by weight unless otherwise stated.

EXAMPLE 1

6-Ethoxycarbonyl-7-methyl-1,2,4-triazolo[2,3-a]pyrimidine was prepared by the method described in Chemical Abstracts Vol 54 (1960) at 11039c (Shirakawa Kenzo). To 10.3 g of this ester was added 12.1 g of 2-hexyldecanol and 10 drops of tetrabutyl titanate and the mixture was stirred at 165° C. for 50 hours. The ethanol produced by the transesterification was allowed to distil out of the reaction mixture, and during the course of the reaction further additions of 5 drops of tetrabutyl titanate were made after 24 hours and 30 hours respectively.

The reaction mixture was cooled and extracted with petroleum ether and the petroleum solution was washed with dilute acid and water and the solvent was removed by distillation. The product was further purified by elution with petroleum ether/ethyl acetate (4:1) from a chromatographic column comprising silica gel (100 g). 16.0 g of liquid product was obtained having the structure:

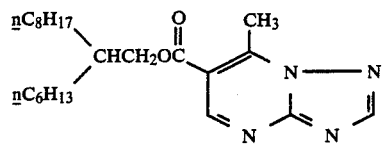

The ability of this compound to extract copper from aqueous solutions containing chloride ion was investigated by the following general method:

An aqueous solution was prepared which was 0.1M in cupric chloride (6.35 gpl copper), and 0.1M in hydrochloric acid and which contained 700 gpl of calcium chloride dihydrate. This solution was then agitated for 1.5 minutes with an equal volume of a solution which was a 0.2M solution of the extractant in SOLVESSO 150. The layers were allowed to separate and settle, and were separately analysed for copper content. The transfer of copper from the aqueous to the organic phase was calculated as the percentage of the total copper present. The transfer of hydrochloric acid from the aqueous solution into the organic solution was calculated as the percentage of ligand that was protonated. The test was repeated using different molarities of hydrochloric acid and different concentrations of calcium chloride.

The stripping of the extractant was demonstrated by shaking the loaded organic solution for 1.5 minutes with 12 times its volume of water, and in each case more than 98% of the copper present in the loaded organic solution was found to be stripped.

The results are presented in Table 1. The results show that the ligand has excellent freedom from transfer of acid even at high chloride ion/acid concentrations, and that its affinity for copper is highly dependent on the concentration of chloride ion in the aqueous phase with which it is contacted, making it ideal for the transfer of copper from aqueous solutions of high chloride ion concentration to aqueous solutions of low chloride ion concentration.

TABLE 1

| Product of Ex. No | Solvent | HCl (Molarity) | CaCl$_2$.2H$_2$O (g/l) | % Uptake from 0.1 M CuCl$_2$ Copper | HCl |
|---|---|---|---|---|---|
| 1 | SOLVESSO 150 | 0.1 | 250 | >1 | 0 |
| | | 0.1 | 700 | 80 | 0 |
| | | 1.0 | 250 | 14 | 0 |
| | | 1.0 | 700 | 83 | 2 |

EXAMPLES 2-5

The isodecanol and tridecanol used in these Examples were the commercially available mixtures of primary aliphatic alcohols manufactured by carbonylation of mixed olefins.

A mixture of highly branched primary alcohols of formula COHOH having the general structure (2) was prepared by boiling a mixture of isodecanol (223 g), potassium hydroxide (15 g) and water (16 g) under reflux below a Dean-Stark trap. As water collected in the trap the temperature of the reaction mixture rose to 236 Deg. Celsius. Heating at this temperature was continued for 3 hours when it was shown by gas chromatography that 60% of the isodecanol had been converted. The mixture was cooled, washed twice with 200 ml portions of water, and then distilled, the fraction boiling at 132-142 Deg. Celsius at 0.05 mm of mercury being collected.

In similar fashion a mixture of highly branched primary alcohols of formula $C_{26}H_{63}OH$ having the general structure (2) was prepared from tridecanol. In this case 0.7 g of lead silicate catalyst prepared as described in British Pat. No. 1,528,705 was included in the reaction mixture as a catalyst. The product distilled at 164-180 Deg. Celsius at 0.07 mm of mercury pressure.

The transesterification procedure described in Example 1 was used to react in turn, isooctadecanol, 2-octyldodecanol and the alcohols prepared as described above, with 6-ethoxycarbonyl-7-methyl-1,2,4-triazolo[2,3-a]pyrimidine so as to give the compounds or mixtures of compounds listed below. In this list the prefix m-denotes "mixed" and the prefi b-denotes "branched". The purities of the products of Examples 2 and 3 were measured by gas-chromatography and the purities of the products of Examples 4 and 5 by potentiometric titration with perchloric acid in acetic acid/acetic anhydride solution.

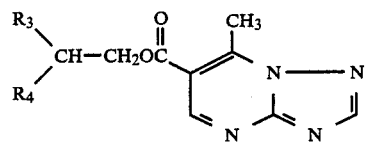

Example 2; $R_3=b-C_7H_{15}$, $R_4=b-C_9H_{19}$, purity 97%, bp 210-220 Deg. Celsius/0.05 mm Example 3; $R_3=n-C_8H_{17}$, $R_4=n-C_{10}H_{21}$, purity 93%

Example 4; $R_3=mb-C_8H_{17}$, $R_4=mb-C_{10}H_{21}$, purity 92%

Example 5; $R_3=mb-C_{11}H_{21}$, $R_4=mb-C_{13}H_{17}$, purity 87%

Each extractant was dissolved in SOLVESSO 150 so as to give a 0.2M solution, and compared with the Product of Example 1 by carrying out the same tests as were used in Example 1 with the results listed in Table 2 below.

TABLE 2

| Product of Example No. | HCL (Molarity) | CaCl$_2$2H$_2$O g/l | % Uptake from 0.1 M CuCl$_2$ Copper | HCl |
|---|---|---|---|---|
| 2 | 0.1 | 250 | 5 | 0 |
| | 0.1 | 700 | 74 | 0 |
| | 1.0 | 700 | 80 | 0 |
| 3 | 0.1 | 250 | 3 | 0 |
| | 0.1 | 700 | 68 | 0 |
| | 1.0 | 700 | 74 | 0 |
| 4 | 0.1 | 250 | 1 | 0 |
| | 0.1 | 700 | 78 | 0.5 |
| | 1.0 | 700 | 78 | 2.0 |
| 5 | 0.1 | 250 | 0 | 0 |
| | 0.1 | 700 | 80 | 0.5 |
| | 1.0 | 700 | 80 | 0 |

The results show that the Products of Examples 2-5 have freedom from acid transfer similar to the Product of Example 1, and that like the Product of Example 1 they extract copper efficiently from aqueous solutions of high chloride ion concentration, but have very little affinity for copper when in contact with aqueous solutions of low chloride ion concentration.

The solubility of the copper complexes formed by the extractants, and hence the concentrations at which they can be usefully employed, was investigated as follows. Solutions of each extractant were prepared, each at several different concentrations in SOLVESSO 150, and each was heavily loaded with copper by successive contact with two equal volumes of an aqueous feed solution which was 0.8 molar in copper (II) and 10 molar in chloride ion. If no separation or precipitation of copper complex occurred, the organic solution was separated and reexamined after 2 weeks. In this way it was found that the Products of Examples 1 and 2 could be used at concentrations up to 0.2 molar, and the Product of Example 3 could be used at concentrations up to 0.3 molar, and the Products of Examples 4 and 5 could be used at concentrations at least up to 0.4 molar, which was the highest concentration examined, without any separation of copper complex from the organic solution occurring. The results show that increasing the number of carbon atoms in the saturated chains attached to the triazolopyrimidine nucleus, and the degree of brancing of these chains, increases the solubility of the corresponding copper complex formed by the extractant.

We claim:

1. A compound of the formula

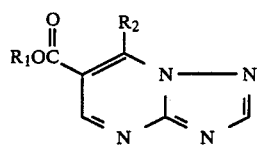

wherein R1 is a hydrocarbyl group having from 1 to 35 saturated atoms and R2 is hydrogen or a hydrocarbyl group containing from 1 to 35 carbon atoms, provided that R1 and R2 taken together contain a total of from 5 to 35 saturated carbon atoms.

2. A compound according to claim 1 wherein R1 is of the formula

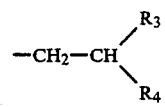

wherein R3 and R4 are both alkyl groups and R3 has two fewer carbon atoms than R4.

3. A compound according to claim 1 wherein R1 and R2 taken together have a total of from 16 to 35 saturated carbon atoms.

4. 6-(2-hexyldecanoxy)carbonyl-7-methyl-1,2,4-triazolo(2,3-a)pyrimidine.

5. A compound or a mixture of compounds according to claim 2 wherein R2 is methyl and R1 has 18 carbon atoms.

6. A mixture of compounds according to claim 2 wherein R2 is methyl and R1 has 20 carbon atoms.

7. A mixture of compounds according to claim 2 wherein R2 is methyl and R1 has 26 carbon atoms.

* * * * *